United States Patent [19]

Bauerfeind et al.

[11] Patent Number: 5,337,733
[45] Date of Patent: Aug. 16, 1994

[54] TUBULAR INSERTING DEVICE WITH VARIABLE RIGIDITY

[76] Inventors: Peter Bauerfeind; Herbert Bauerfeind, both of Pettenkoferstrasse 4, 8264 Waldkraiburg, Fed. Rep. of Germany

[21] Appl. No.: 849,027
[22] PCT Filed: Sep. 11, 1990
[86] PCT No.: PCT/EP90/01532
§ 371 Date: Apr. 22, 1992
§ 102(e) Date: Apr. 22, 1992
[87] PCT Pub. No.: WO91/05507
PCT Pub. Date: May 2, 1991

[30] Foreign Application Priority Data
Oct. 23, 1989 [DE] Fed. Rep. of Germany ....... 3935256

[51] Int. Cl.$^5$ .............................. A61B 1/00; A61M 25/01
[52] U.S. Cl. ........................................ 128/4; 604/281; 604/282
[58] Field of Search ............... 604/280, 281, 282, 156; 128/657, 772, 4, 6; 385/115, 118; 606/194

[56] References Cited
U.S. PATENT DOCUMENTS

| 4,141,364 | 2/1979 | Schultze ................ 128/4 X |
| 4,551,140 | 11/1985 | Shinohara ............ 604/280 X |
| 4,696,544 | 9/1987 | Costella . |
| 4,717,379 | 1/1988 | Ekholmer ............ 604/280 X |
| 4,815,450 | 3/1989 | Patel ....................... 128/6 |
| 4,961,738 | 10/1990 | Mackin ................ 128/6 X |

Primary Examiner—Richard J. Apley
Assistant Examiner—John P. Leubecker
Attorney, Agent, or Firm—Woodard, Emhardt, Naughton, Moriarty & McNett

[57] ABSTRACT

The inserting means comprises a flexible insertion part (14) adapted to be pushed into an object to be examined, especially the human colon (60) and including, between an inner wall (16) and an outer wall (18), an intermediate space (20) sealed towards the outside. The outer wall (18) is formed by a flexible hose which, however, cannot be inflated like a balloon by the fluid in the intermediate space (20). The inner wall (16) of the insertion part (14) likewise is formed by a hose; the latter is deformable radially inwardly by fluid introduced into the intermediate space (20) and can be caused to lie against the outer wall (18) by evacuation of the intermediate space (20). The insertion part (14) can be rendered rigid in any desired position by evacuating the intermediate space (20). It is easy to insert the corresponding instrument, e.g. the colonoscope into the object to be examined through the insertion part (14) thus fixed. The insertion part (14) becomes flexible again when the intermediate space (20) is filled with fluid, such as air.

10 Claims, 6 Drawing Sheets

TUBULAR INSERTING DEVICE WITH VARIABLE RIGIDITY

BACKGROUND OF THE INVENTION

The invention relates to an inserting means for tubular, fiberoptic instruments, especially colonoscopes, gastroscopes, and the like, comprising a grip part and a flexible insertion part adapted to be pushed into an object to be examined, especially the human colon and including, between an inner wall and an outer wall, at least one intermediate space which is sealed outwardly and into which a fluid can be introduced. The outer wall of the insertion part is formed by a flexible hose which, however, is not inflatable like a balloon by the fluid in the intermediate space. The inner wall of the insertion part likewise is formed by a hose, and The intermediate space contains support elements through which the inner wall and the outer wall are mutually supported when the pressure in the intermediate space fails to reach a predetermined value.

An inserting means of this kind is known from U.S. Pat. No. 4,815,450. There the intermediate space contains ball shaped support elements between the inner and outer walls of the insertion part which elements are freely disposed and therefore movable in the intermediate space. As a consequence, the support elements may become shifted in the intermediate space and consequently do not always reliably fulfill their task of stiffening the insertion part when there is a vacuum in the intermediate space. The user therefore cannot rely on the inserting means keeping a particular desired configuration during a particular manipulation of a colonoscope or the like.

As is known, for example, from U.S. Pat. No. 4,696,544, there are fields of application for tubular fiberoptic instruments outside of the medical field, too, such as for examining pipelines, vessels, and machine parts. The term "object to be examined" is to be understood accordingly in the context of the present invention.

For inserting colonoscopes, also inserting means are being used which have a one-piece slip tube which is of great flexural stiffness as compared to the corresponding colonoscope and permits only relatively minor elastic bending. The inner diameter of such a slip tube for a colonoscope having an outer diameter of 15 mm, for instance, is barely 16 mm so that the colonoscope can be pushed through easily any time. The outer diameter of the slip tube is 19 mm, for example. The insertion part is 40 cm long. The length of the associated colonoscope usually is between 130 and 180 cm. A distal end portion, approximately 10 cm long, of the colonoscope usually can be moved in four directions (up/down and left/right) by means of setting wheels supported at the proximal end.

The physician performing an examination or treatment pushes the colonoscope from the anus into the colon. The colonoscope must be advanced up to the cecum in order to permit full examination of the colon. In doing that, the direction of movement of the colonoscope can be determined by its movable distal end portion. However, at the bends of the colon, namely at the sigmoid and especially at the two colon flexures, problems regularly occur, including the risk of injury, pain to the patient, and cramp-like contractions of the colon, even up to the impossibility of continuing the examination. These problems are related to the fact that the colon is soft and fixed only relatively little in the abdomen. After a deflection, the principal direction of the force by which the colonoscope is advanced no longer is towards the distal end of the colonoscope but instead towards the readily yielding wall of the colon, a fact which is unpleasant for the patient. Therefore, the cecum cannot be reached in about 10 to 15% of all cases.

These difficulties can be overcome only in part by the customary inserting means since they are suitable for guiding the colonoscope only through the rectum and, at best, the sigmoid and the colon descendens. Yet the problems described continue to exist at the left colon flexure, at the latest. Moreover, many patients already find it unpleasant that the sigmoid is forced into an almost rectilinear shape by the slip tube since the configuration of the slip tube is not variable at random. Due to the great stiffness of the slip tube there is a risk of perforating the colon if the slip tube is handled carelessly.

A mechanical-pneumatical manipulation system for colonoscopes is known from DE 36 05 169 A1 where an inserting means is intended to make it easier for the physician and the patient to introduce a colonoscope. This inserting means, too, comprises a flexible slip tube into which the colonoscope can be slipped. A balloon or group of balloons of highly flexible material is arranged on the slip tube. In vented condition the balloon or group of balloons lies in close contact with the slip tube; in inflated condition the balloon or group of balloons is to find support in the surroundings, i.e. on the intestinal wall, and the shaft of the colonoscope is to be movable forwardly or backwardly with the aid of the mechanics. A second group of balloons firmly mounted on the colonoscope shaft are vented when the colonoscope is to be displaced with respect to the slip tube which is supported in the vicinity and they are inflated when the slip tube is to be displaced together with its balloon or group of balloons. The slip tube includes longitudinal passages one of which is intended to house pressure and vacuum conduits and another one to receive a mechanical push-pull system.

This inserting means with an inflatable balloon or a group of such balloons arranged at the outside cannot very much ease the insertion of a colonoscope into the human intestine because the intestine reacts in the same manner by spastic and painful contractions to every extension, regardless of whether it is caused by an unprotected colonoscope or by one or more blown up balloons. Such contractions also occur distally of the colonoscope and make it difficult to push it on. The known inserting means is not suited for non-medical objects of examination, such as parts of machinery which may have sharp-edged inner contours because a balloon assembly on the flexible slip tube is susceptible of damage.

The same applies mutatis mutandis to a device known from DE 28 23 025 C2 for transferring a colonoscope where the distal end of the colonoscope is connected by a thin, overturned hose to the distal end of a conical tube adapted to be introduced into the human anal ring. A housing enclosing the colonoscope and provided with a connecting socket can be screwed on to the proximal end of the tube. When a pressure medium is introduced through the connecting socket a portion of the hose located between the two hose ends is pushed into the large intestine while, at the same time, it turns inside out, pulling along the colonoscope. The latter thus is to move into the intestine by being pulled rather than pushed. As the hose advances, its interior is to turn inside out progressively so that then it will form an outer hose portion which does not move with respect to the mucous membrane of the intestine. However, that may also cause painful spastic intestinal contractions. Even if it is possible with this known device to advance a colonoscope far enough, especially all the way to the cecum, it is still not possible to leave the hose in the intestine and use it as an aid for the renewed insertion of the colonoscope if the latter has been pulled out preliminarily, for example to remove a larger polyp. The hose which can be overturned and consequently must be thin is not suitable for technical applications because it can tear easily at sharp edges and protrusions of the object under examination.

SUMMARY OF THE INVENTION

It is the object of the invention to devise an inserting means for tubular fiberoptic instruments, especially colonoscopes, gastroscopes, and the like in such a manner that it substantially facilitates the complete and multiple insertion, if required. of such an instrument all the way to the end of the object to be examined and, in case of medical examinations, makes this more tolerable for the patient and easier for the physician.

Starting from an inserting means of the kind described initially, this object is met, in accordance with the invention, in that some of the support elements are firmly arranged at the outside of the inner wall and the remainder of the support elements are firmly arranged at the inside of the outer wall.

The support elements may be warts, helices, fins, and the like. The firm or fixed arrangement of the support elements can result from one-piece manufacture of the support elements and the associated inner or outer wall, or from gluing, fusing, or vulcanizing separately made support elements to the walls. The inner and outer walls together present an insertion part which can be rendered rigid in any desired bent shape, e.g. adapted to the sigmoid and even to the two colon flexures, by evacuation of the intermediate space to such a degree that the support elements of the inner wall abut against those of the outer wall. A fiberoptic instrument, especially a colonoscope can be introduced with relative ease through the insertion part thus deformed and fixed. If fluid is again introduced into the intermediate space the insertion part regains its original flexibility.

The inner wall preferably is deformable radially inwardly by fluid introduced into the intermediate space, thereby coming to lie against a sheath surface of a fiberoptic instrument, especially a colonoscope passed through the inserting means. The inner wall of the insertion part thus can be pressed firmly against an instrument, especially a colonoscope passed through the inserting means by introducing a pressurized fluid, such as compressed air into the intermediate space without blowing up the outer wall. In this state the inserting means still is flexible and can be advanced together with the fiberoptic instrument due to its temporary fixed connection to the same. Thus it is no problem to reach the end of the area to be examined, for example the cecum by alternatingly pushing forward the instrument alone and the instrument together with the inserting means.

Particularly solid interlocking and thus high bending resistance of the evacuated insertion part results if the support elements which are arranged at the outside of the inner wall each engage in a gap between support elements provided at the inside of the outer wall.

The intermediate space can be subdivided into a plurality of chambers adapted to be evacuated and pressurized, if needed, in common or separately. Such chambers may be separated from each other, for instance, by welding seams or other seams interconnecting the inner and outer walls in the manner of quilted seams. The chambers may extend rectilinearly or helically along the insertion part. The inner and outer walls can form uniform wall sections between the chambers.

In a preferred embodiment of the invention the support elements which are firmly arranged at the inner wall of the insertion part are of sleeve-like design and each engage between two adjacent sleeve-like support elements which are firmly arranged at the outer wall of the insertion part. With this embodiment the insertion part can be stiffened especially effectively by evacuating the space intermediate its inner and outer walls.

The embodiment described above may be developed further in that the support elements arranged at the inner wall are designed to be radially expansible and compressible by slots formed over part of their axial length. Due to this measure the slotted support elements arranged at the inner wall snugly engage the support elements of the outer wall upon evacuation. Such slots further make it possible to bend the insertion part around particularly narrow radii.

On the other hand, it is advantageous if the support elements arranged at the outer wall comprise a nonextensible annular bead at both ends which covers the slots of the two adjacent support elements over part of their axial extension only so that all parts of the intermediate space are interconnected through at least part of the slots, no matter what the position of the insertion part. Such annular beads have the additional advantage of counteracting any tendency of the outer wall to become inflated when positive pressure prevails in the intermediate space between the inner and outer walls.

The stiffening of the insertion part, with the intermediate space evacuated, can be enhanced by providing the support elements arranged at the inner wall with an external corrugation and the support elements arranged at the outer wall with a corresponding internal corrugation. The corrugations which thus are located radially opposite each other become interlocked when the intermediate space is evacuated so that the insertion part is fixed in form lock in the position it had just before evacuation of the intermediate space.

BRIEF DESCRIPTION OF THE DRAWINGS

Embodiments of the invention will be described in greater detail below with reference to diagrammatic drawings, in which.

DESCRIPTION OF THE PREFERRED EMBODIMENTS

Figure 1:
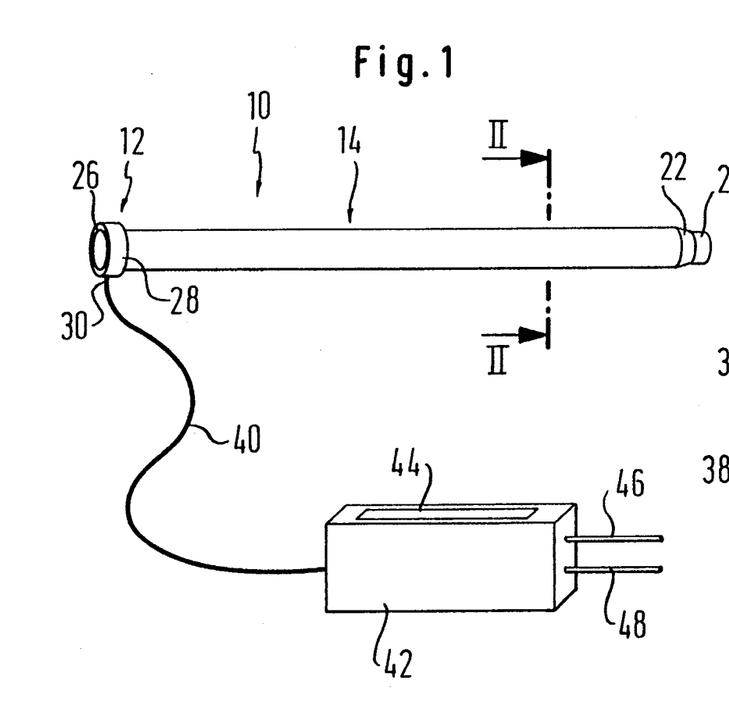
FIG. 1 is an overall view of an inserting means according to the invention comprising a insertion part and associated equipment.
Figure 2:
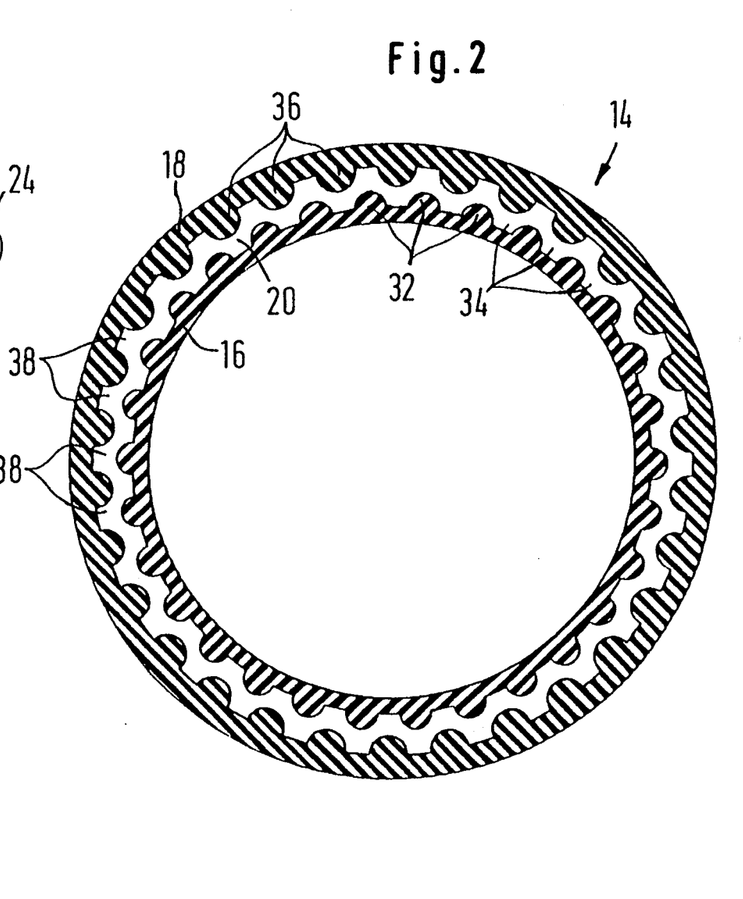
FIG. 2 shows the cross section II—II through the insertion part in inflated state and on greatly enlarged scale.

The main components of the inserting means 10 illustrated in FIGS. 1 and 2 are a grip part 12 and an insertion part 14. The insertion part 14 comprises an inner wall 16, an outer wall 18, an annular intermediate space 20 formed between said walls, a distal end portion 22, and finally a distal guide ring 24. At the grip part 12 and at the distal end portion 22 the inner wall 16 is connected tightly to the outer wall 18 whereby the intermediate space 20 is sealed.

According to FIG. 1 the grip part 12 substantially consists of an inner sleeve 26 to which the inner wall 16 is tigthly secured and an outer sleeve 28 to which the outer wall 18 is tightly secured. The inner wall 16 and the outer wall 18, for instance, may be vulcanized, glued, and/or tightly clamped to the respective sleeve 26 or 28. The two sleeves 26 and 28 are tightly connected to each other at their proximal end portions, for example by being threaded together.

A connection 30 for supply and withdrawal of fluid into and out of the intermediate space 20 is located at the outer sleeve 28 or in a connecting area between the outer sleeve 28 and the inner sleeve 26. A slide ring sealing each is suitably arranged at the inside of the inner sleeve 26 of the grip part 12 and at the distal end portion 22 of the insertion part 14 to provide sealing against the associated fiberoptic instrument. An additional suction and/or rinsing conduit may open into the interior of the inner sleeve 26 in order that air or secretion from a body organ under examination can be sucked off or a rinsing liquid be introduced through the inserting means.

The inner wall 16 and the outer wall 18 each are formed of a tubular film of pliable plastic material which is physically tolerable. In the embodiment illustrated in FIG. 2 the inner wall 16 is less thick than the outer wall 18 and consequently can be deformed radially inwardly with ease when positive pressure is generated inside the intermediate space 20; the outer wall 18 on the other hand is so solid and reinforced with fibers, if desired, that it does not become inflated by a pressure prevailing in the intermediate space 20 which already produces quite some deformation of the inner wall 16.

According to FIG. 2, support elements 32 are disposed evenly distributed at the outside of the inner wall 16; gaps 34 are left between them. In corresponding manner support elements 36 and gaps 38 are arranged at the inside of the outer wall 18 in such manner that each support element 32 is located radially opposite a gap 38 and each support element 36 is located radially opposite a gap 34. As long as ambient pressure prevails in the intermediate space 20 the support elements 32 and 36 touch each other only lightly or not at all. This condition is represented in FIG. 2. However, each support element 32 enters into a gap 38 and each support element 36 enters into a gap 34 as the intermediate space 20 is evacuated more or less. Hereby the insertion part 14 is rendered rigid in any desired configuration which it had adopted prior to the evacuation.

To use the inserting means according to the invention, the connection 30 is hooked up via a hose 40 to a control apparatus 42 of conventional type which, for example, connects the hose selectively to a compressed air conduit 46 or a vacuum conduit 48 by actuation of a rocker-type switch 44. A commercially available colonoscope 50 is inserted, distal end 52 first, into the proximal end of the guide tube 10 and pushed through the grip part 12 as well as the insertion part 14.

The further manipulation of the inserting means 10 and the colonoscope 50 takes place at the patient and is illustrated in FIGS. 3a to 3f. In each case the joint presentation of the insertion part 14 and the colonoscope 50 as a thick line means that air (or another fluid) has been fed under pressure into the intermediate space 20, and thereby the inner wall 16 has been brought into close engagement with the colonoscope 50; the insertion part 14 then is just as flexible as the colonoscope 50. The presentation of the insertion part 14 as a pair of thin lines distinguishable from the colonoscope 50, on the other hand, means that negative pressure prevails in the insertion part 14 at which the inner wall 16 releases the colonoscope 50 for relative shifting movements and is itself firmly engaged with the outer wall 18 so that the insertion part 14 is stiffened.

Figure 3A:
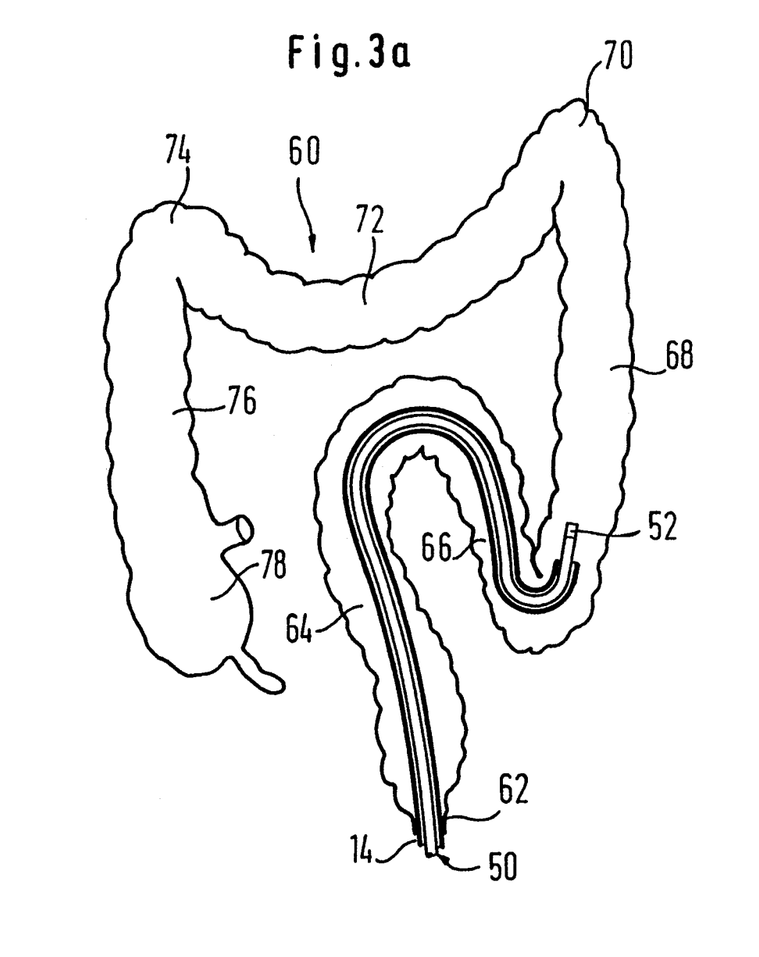
FIGS. 3a to f show six consecutive manipulations of a colonoscope with an inserting means.

According to FIG. 3a the colonoscope 50, together with the pliable insertion part 14 firmly in contact with it, is pushed into the colon 60, beginning from the anus 62, through the rectum 64 up to the transition from the sigmoid 66 to the colon descendens 68. The insertion part 14 is rendered rigid in this position by evacuating its intermediate space 20.

Figure 3B:
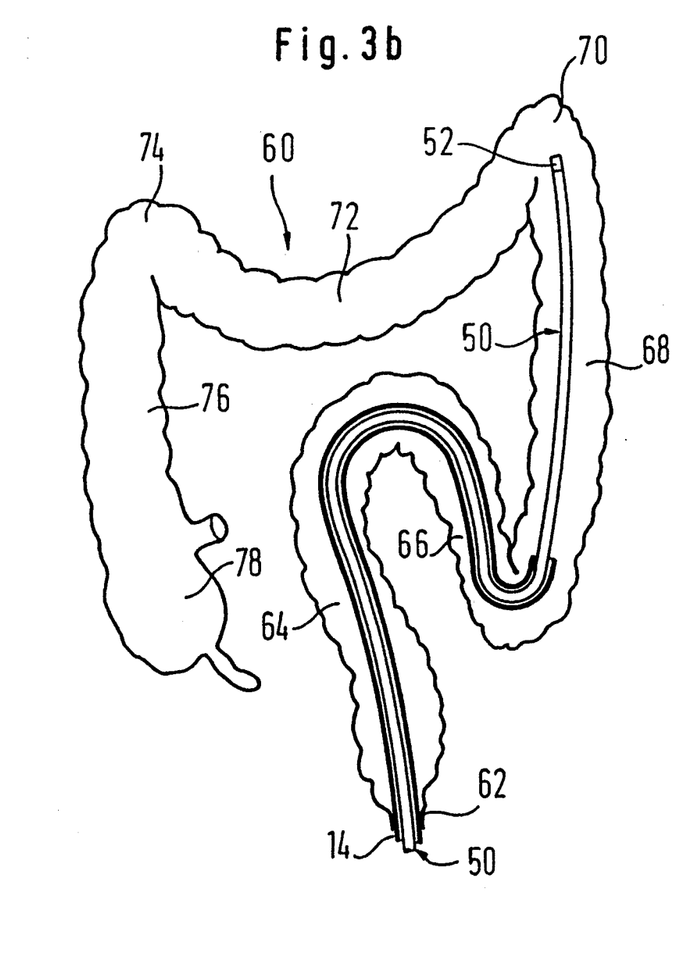

According to FIG. 3b the endoscope 50 is advanced up to the left colon flexure 70 through the inserting means 10 which has the rigidified insertion part 14.

Figure 3C:
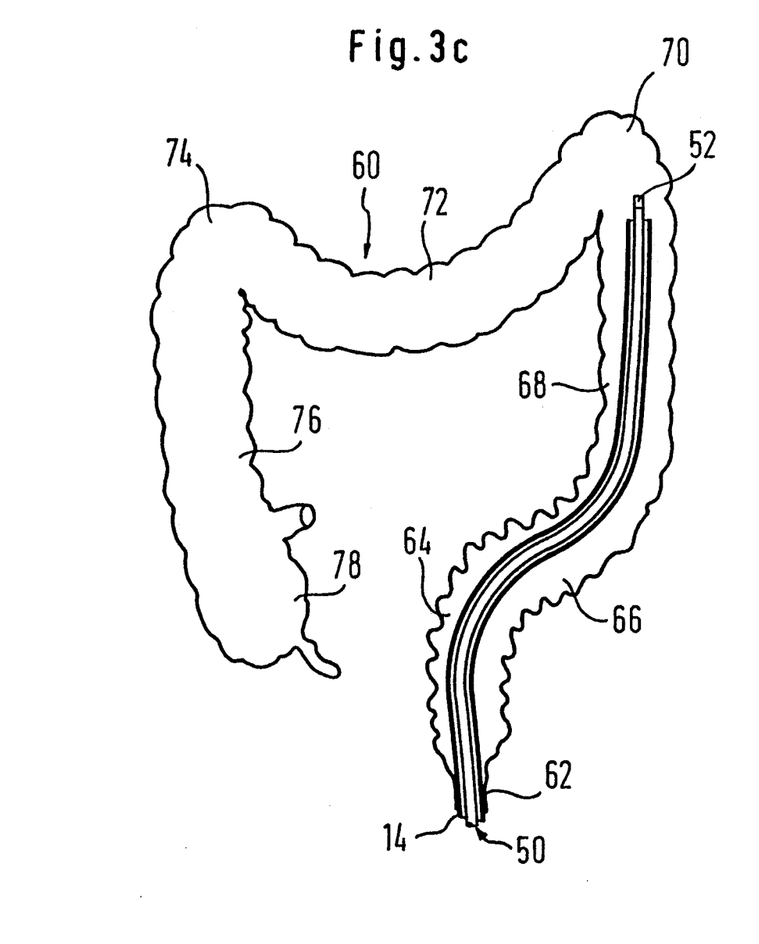

According to FIG. 3c the stiffening of the insertion part 14 is cancelled by introducing compressed air into its intermediate space 20; the sigmoid 66 is straightened somewhat, and the insertion part 14, too, is pushed on to the left colon flexure 70.

Figure 3D:
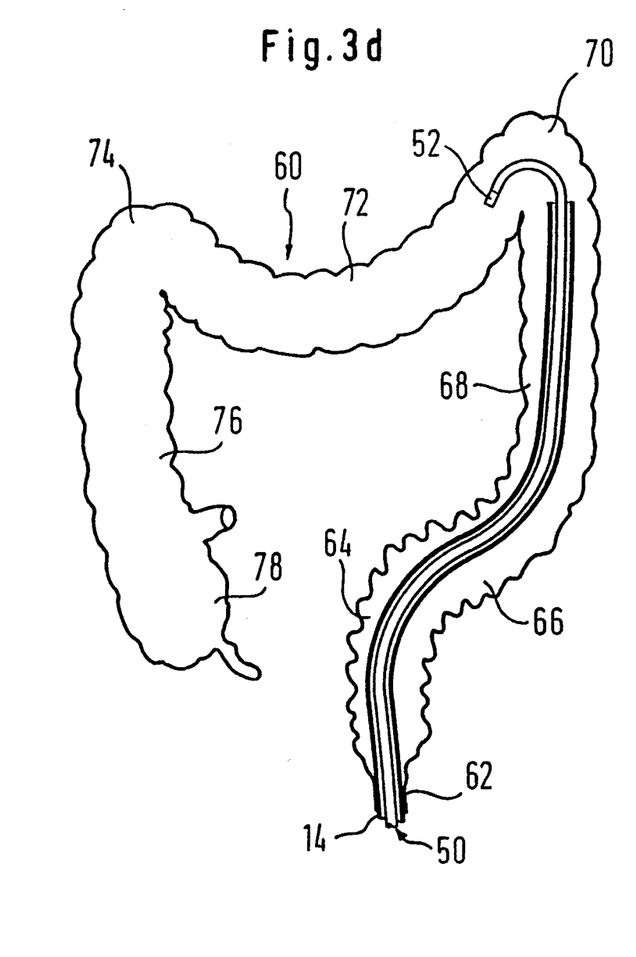

In the position according to FIG. 3d the insertion part 14 is rigidified once more and the colonoscope 50 is pushed through the left colon flexure 70.

Figure 3E:
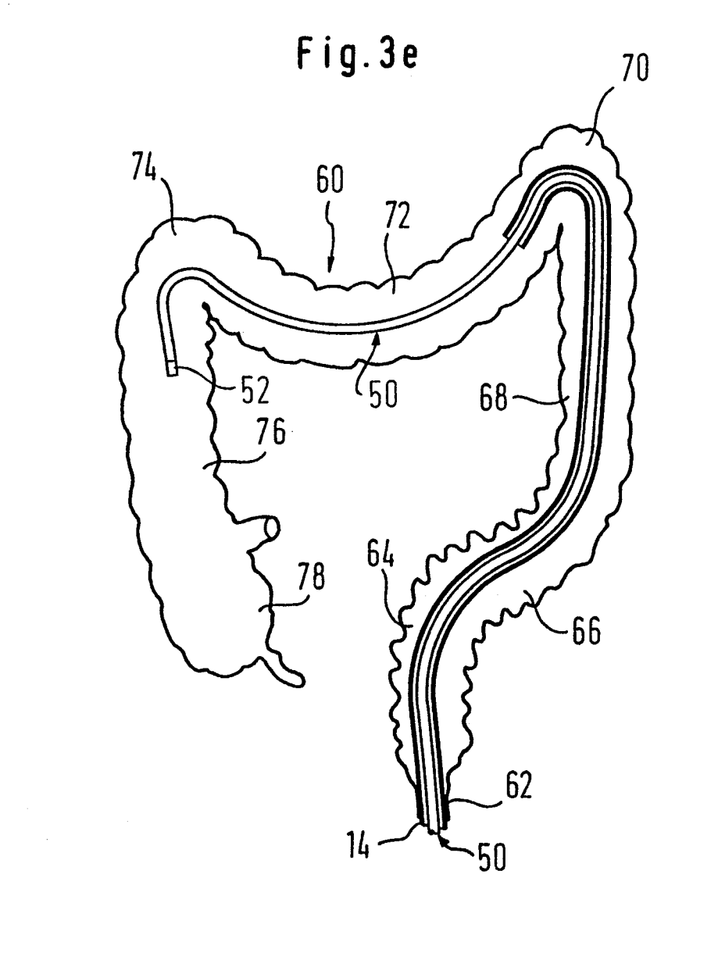

According to FIG. 3e the stiffening of the insertion part 14 has been cancelled again; the insertion part 14 now is pushed up beyond the left colon flexure 70 and then rendered rigid once more; subsequently the endoscope 50 is advanced up to the right colon flexure 74 and beyond.

Figure 3F:
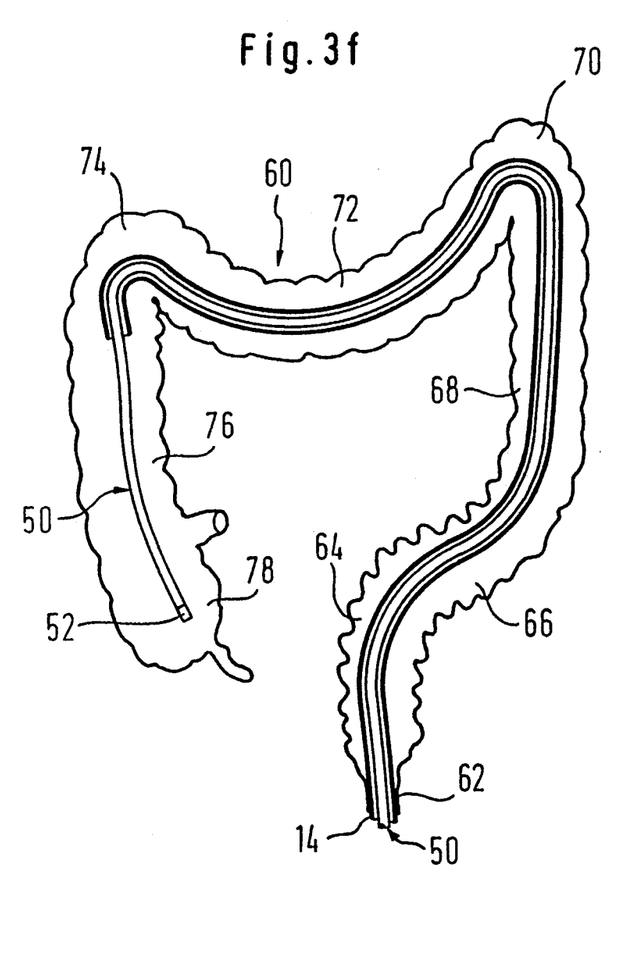

According to FIG. 3f the stiffening of the insertion part 14 is given up again; the insertion part 14, too, is pushed up beyond the right colon flexure 74 and then stiffened again so that the colonoscope 50 now can be advanced further all the way into the cecum 78.

In each of the positions described and in all intermediate positions of the inserting means 10 the colonoscope 50 can be pulled out completely, for example in order to carry a tumor to the outside which has been removed by a sling but cannot be passed through the colonoscope 50. Subsequently the colonoscope 50 can be reinserted through the inserting means 10 which remained in stiff condition inside the colon 60, and further tumors can be excised and moved to the outside, if necessary.

Figure 4:
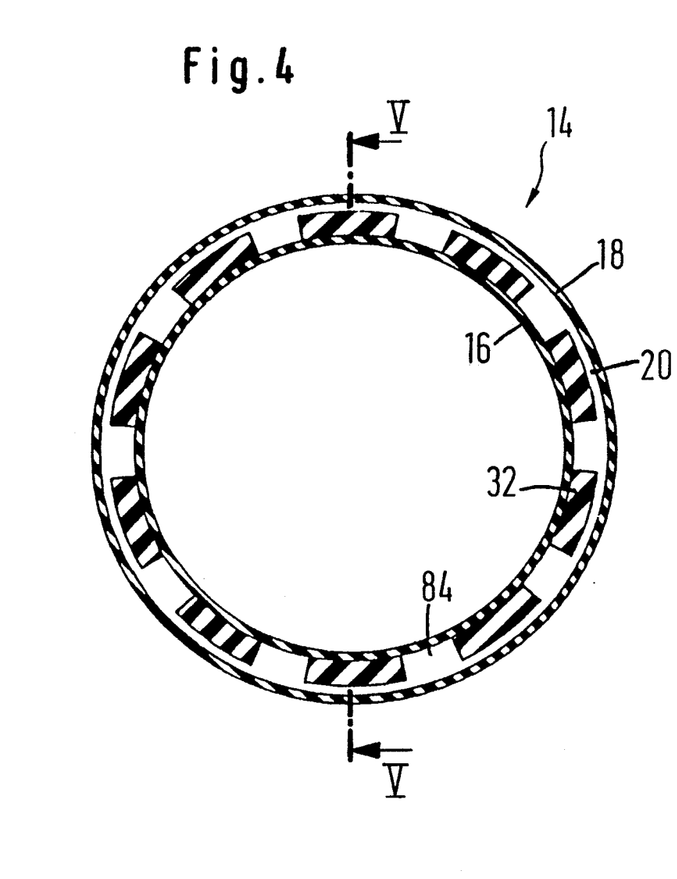
FIG. 4 shows a second embodiment of an insertion part according to the invention in cross section IV—IV of FIG. 5, in inflated state.
Figure 5:
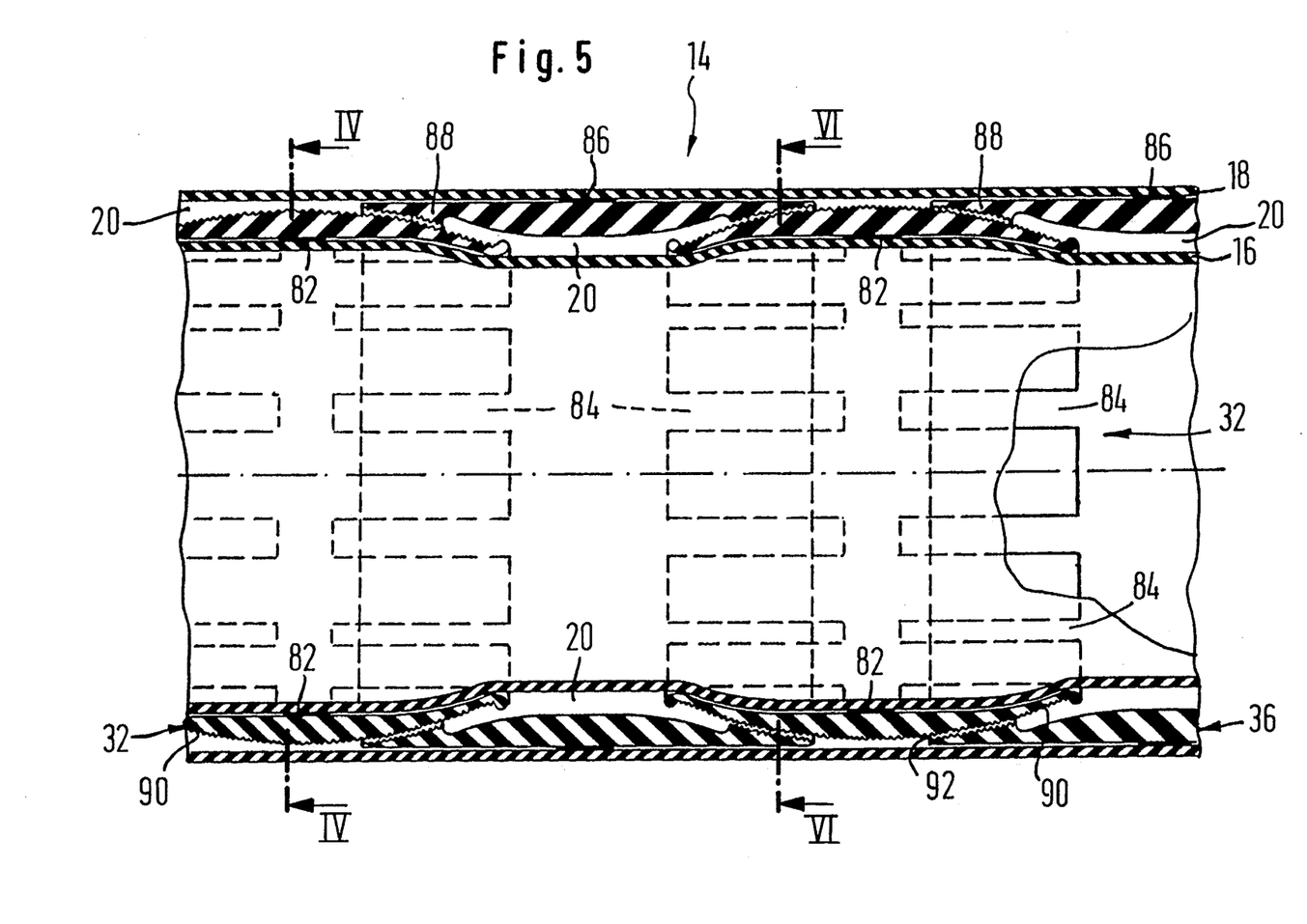
FIG. 5 shows the longitudinal section V—V of FIG. 4 still more enlarged.
Figure 6:
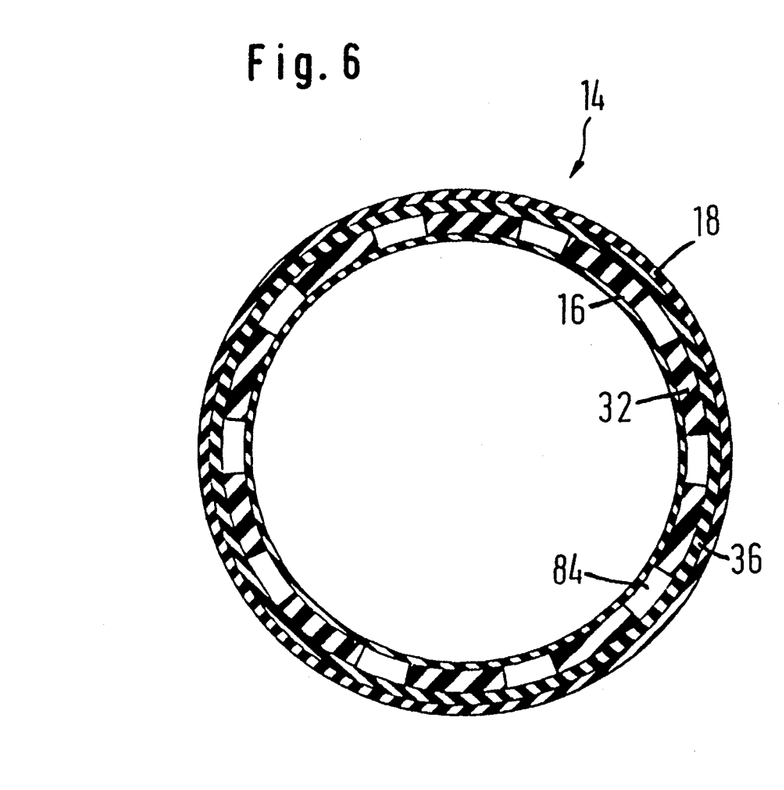
FIG. 6 shows the cross section VI—VI of FIG. 5.

The preferred embodiment of the invention shown in FIGS. 4 to 6 has ring- or sleeve-like support elements 32 arranged at the outside of the inner wall 16 which are each fastened to the inner wall 16 by an annular weld or glue attachment 82 centrally located on each element. Each support element 32 includes axis parallel slots 84 starting from both its face ends and each extending for almost half the axial width of the support element 32. The slots 84 are of such width that the annular support elements 32 can be highly compressed and also widened in radial direction in their end regions.

Ring- or sleeve-like support elements 36 are arranged at the inside of the outer wall 18 and likewise each fastened to the outer wall 18 by an annular weld or glue attachment centrally located on each element. Each support element 32 enters axially between two adjacent support elements 36; in corresponding manner each support element 36 extends over the two adjacent support elements 32 for part of their axial length, e.g. about one third thereof. The support elements 36 are not slotted but instead provided at each end with an annular bead 88 which is only slightly extensible or not at all.

The support elements 32 each have a spherical outer face provided with corrugations 90; the support elements 36 are of complementary spherical shape at the inside of their annular beads 88 and provided with corresponding corrugations 92. When the intermediate space 20 again defined between the inner wall 16 and the outer wall 18 is evacuated the corrugations 90 and 92 of overlapping support elements 32 and 36 engage each other, thus fixing the support elements in the position they held at the beginning of the evacuating process. The slots 84 form longitudinal channels which make sure that the intermediate space 20 between the inner 16 and outer walls 18 can be evacuated without any difficulty over the full length of the insertion part 14. Due to the interlocking corrugations 90 and 92 the insertion part 14 is given a stiffness, in the evacuated state of its intermediate space 20, which is many degrees higher than the stiffness, which is very low as such, of the inner wall 16 and the outer wall 18. This rigidness can be achieved with the insertion part 14 in any desired bent configuration.

What is claimed is:

1. An inserting device (10) tubular fiberoptic instruments comprising
   a flexible insertion part (14) adapted to be pushed into an object to be examined, including
      an inner wall (16) being formed by a hose that is radially expandable,
      an outer wall (18) being formed by a flexible hose that is not radially expandable,
      said inner wall (16) and outer wall (18) defining at least one sealed intermediate space (20) into which fluid can be introduced, and
      support elements (32, 36) contained within said intermediate space (20) and being fixedly arranged on the outside of the inner wall (16) and on the inside of the outer wall (18) to mutually cooperate for adding rigidity to the inserting device when the pressure in the intermediate space (20) is below ambient pressure.

2. The inserting device as claimed in claim 1, characterized in that the support elements (32) which are arranged at the outside of the inner wall (16) each engage in a gap (38) formed between support elements (36) at the inside of the outer wall (18).

3. The inserting device as claimed in claim 1, characterized in that the support elements (32, 36) extend around the circumference of the outside of the inner wall (16) and around the circumference of the inside of the outer wall (18) as continuous reinforcements of the inner (16) and outer walls (18).

4. The inserting device as claimed in claim 3, characterized in that the support elements (32) which are fixedly arranged at the inner wall (16) of the insertion part (14) are formed as sleeves, each engaging two adjacent sleeves that form support elements (36) which are firmly arranged at the outer wall (18) of the insertion part (14).

5. The inserting device as claimed in claim 4, characterized in that the support elements (32) arranged at the inner wall (16) are designed to be radially expansible and compressible by slots (84) over part of their axial extension.

6. An inserting device (10) for tubular fiberoptic instruments comprising
   a flexible insertion part (14) adapted to be pushed into an object to be examined, including
      an inner wall (16) being formed by a hose that is radially expandable,
      an outer wall (18) being formed by a flexible hose that is not radially expandable,
      said inner wall (16) and outer wall (18) defining at least one sealed intermediate space (20) into which fluid can be introduced, and
      support elements (32, 36) contained within said intermediate space (20) and being fixedly arranged on the outside of the inner wall (16) and on the inside of the outer wall (18) to mutually cooperate for adding rigidity to the inserting device when the pressure in the intermediate space (20) is below ambient pressure,
   wherein the support elements (32, 36) extend around the circumference of the outside of the inner wall (16) and around the circumference of the inside of the outer wall (18) as continuous reinforcements of the inner and outer walls, and
   wherein the support elements (32) which are fixedly arranged at the inner wall (16) are formed as sleeves, each engaging two adjacent sleeves that form support elements (36) which are fixedly arranged at the outer wall (18), and
   wherein the support elements (32) arranged at the inner wall are designed to be radially expansible and compressible by slots (84) over part of their axial extension, and
   wherein the support elements (36) arranged at the outer wall (18) comprise a non-extensible annular bead (88) each at both ends which covers only part of the axial extension of the slots (84) of the two adjacent support elements (36) so that all parts of the intermediate space (20) communicate with each other through at least part of the slots (84).

7. The inserting device as claimed in claim 1, characterized in that the support elements (32) arranged at the inner wall (16) are formed with corrugations (90) facing the outside, and that the support elements (36) arranged at the outer wall are formed with corresponding corrugations facing the inside.

8. The inserting device as claimed in claim 1, characterized in that the support elements (32, 36) are made integral with the respective inner (16) and outer walls (18).

9. The inserting device as claimed in claim 1, characterized in that the inner wall (16) is deformable radially inwardly by fluid introduced into the intermediate space (20), thereby being adapted to engage a sheath surface of a fiberoptic instrument, especially a colonoscope (50) passed through the inserting device (10).

10. The inserting device as claimed in claim 2, characterized in that the support elements (32, 36) extend around the circumferences as continuous reinforcements of the inner (16) and outer walls (18), respectively.

* * * * *